United States Patent [19]

Donnelly

[11] 4,399,823

[45] Aug. 23, 1983

[54] APPARATUS FOR DETECTING PROBE DISLODGEMENT

[75] Inventor: Michael M. Donnelly, Tipperary, Ireland

[73] Assignee: Air-Shields, Inc., Hatboro, Pa.

[21] Appl. No.: 308,361

[22] Filed: Oct. 5, 1981

[51] Int. Cl.³ .............................................. A61B 5/00
[52] U.S. Cl. .................................... 128/736; 128/1 B; 128/399; 374/163
[58] Field of Search ............ 128/734, 736, 1 B, 275.1, 128/303.1, 303.13–303.14, 399, 908; 374/100–103, 110, 112, 114, 163–164, 172–173; 340/573, 584, 588–589

[56] References Cited

U.S. PATENT DOCUMENTS

| | | | |
|---|---|---|---|
| 3,597,676 | 8/1971 | Moore | 374/112 X |
| 3,781,837 | 12/1973 | Anderson et al. | 128/736 |
| 3,915,003 | 10/1975 | Adams | 374/163 X |
| 4,182,183 | 1/1980 | Funk et al. | 128/303.1 |
| 4,294,263 | 10/1981 | Hochman | 128/736 |
| 4,295,475 | 10/1981 | Torzala | 128/736 |
| 4,322,594 | 3/1982 | Brisson | 128/724 X |
| 4,331,161 | 5/1982 | Patel | 128/736 |

FOREIGN PATENT DOCUMENTS 2045978  11/1980  United Kingdom ............... 128/736

*Primary Examiner*—Lee S. Cohen
*Assistant Examiner*—Angela D. Sykes
*Attorney, Agent, or Firm*—Weiser, Stapler & Spivak

[57] ABSTRACT

A loose probe alarm in which a temperature responsive element (14) arranged for attachment to a body is periodically heated (20, 22, 26) and the effects of self-heating of the temperature responsive element are monitored (32, 36, 38) to determine whether the temperature responsive element has been dislodged from the body. The alarm is arranged to sense during the heating period of the temperature responsive element the difference in the amount of heat dissipated by the temperature responsive element when it remains in contact with the body to which it has been attached and when it has been dislodged from this body.

13 Claims, 4 Drawing Figures

APPARATUS FOR DETECTING PROBE DISLODGEMENT

DESCRIPTION

TECHNICAL FIELD

The present invention relates, in general, to probes and, in particular, to a contact probe arranged for detecting dislodgment of the probe from a body to which it has been attached and apparatus for providing an indication of such dislodgement. Although the invention will be described in connection with a body temperature sensing probe, it will be apparent that the invention has broader application.

BACKGROUND ART

Many probes are in use today to measure or monitor a function of the body to which the probe is attached or to control or influence a body state or condition. For example, the thermal environment of an infant incubator may be regulated by sensing the body temperature of the infant and developing a signal, representative of the infant's body temperature, for controlling the incubator heater. In such an application, it is important that intimate contact, between the skin and the probe contact surface which carries the temperature sensor, be established and maintained. Should the probe become dislodged, resulting in a total or partial loss of contact, the heater will respond to a temperature measurement other than the infant's body temperature.

One approach, currently in use, for detecting probe dislodgement involves using information directly from the function being monitored. A significant deviation in the measurement of a body function may be the result of a significant change in the body function itself or the result of the measuring probe being dislodged from the body. In either case, an indication of the condition should be developed. While such an approach may be adequate for certain applications to sense a complete dislodgement of the probe, a partial dislodgement may produce an inadequate deviation and go unnoticed. Also, in some applications, the function being monitored may not change so appreciably upon probe dislodgement as to produce an adequate indication. For example, in an incubator, the ambient temperature may be approximately equal to the temperature of the infant. Therefore, when a probe attached to the infant becomes dislodged and exposed to the thermal environment of the incubator, there may be very little, if any, immediate change in the output of the temperature sensor.

Another technique which has been suggested for detecting probe dislodgement involves sensing impedance changes due to changing contact conditions between the probe and the body. This approach has met with only limited acceptance. It has been found that various other factors besides loss of contact between the probe and the body affect the impedance. As a result, this technique does not provide adequate reliability.

United States patent application Ser. No. 075,253 filed on Sept. 13, 1979 by Benjamin L. Hochman and United States patent application Ser. No. 088,474 filed by Terence A. Torzala on Oct. 26, 1979 each disclose an optical technique for detecting probe dislodgement. The apparatus disclosed in the Hochman application and the apparatus disclosed in the Torzala application each sense a change in the level of radiation impinging upon the body contact surface of the probe when the probe is dislodged from the body. Although the techniques disclosed in the Hochman and Torzala applications are extremely useful in effectively detecting probe dislodgement, the particular apparatus disclosed in the Hochman and Torzala applications require the addition of optical components to the probe structure and special circuitry to protect against false alarms.

DISCLOSURE OF THE INVENTION

Accordingly, it is an object of the present invention to provide new and improved apparatus for detecting the dislodgement of an article, such as a probe, from a body to which the article has been attached and for developing an indication when such dislodgement occurs.

It is another object of the present invention to provide such apparatus which is reliable in operation, relatively simple in construction, and may be fabricated at reasonable cost.

Apparatus constructed in accordance with the present invention includes a temperature responsive element having a characteristic which varies as a function of its temperature and which is adapted for contact with a body for sensing the proximity of the element to the body. The apparatus also includes means for periodically heating the temperature responsive element and for developing a control signal which varies in accordance with the temperature characteristic of the temperature responsive element. The control signal, thus, is representative of the heating of the element and the heat dissipated from the element. The level of the control signal changes during each periodic heating of the temperature responsive element at a rate dependent upon the dissipation of heat from the temperature responsive element. The apparatus further includes means responsive to the control signal for developing during the period of heating of the temperature responsive element an indication of the proximity of the temperature responsive element to the body.

An additional aspect of the present invention is that when it is applied to a body temperature sensing probe, the temperature responsive element which serves to sense the temperature of the body to which the probe is attached also may serve to sense dislodgement of the probe from the body.

BRIEF DESCRIPTION OF DRAWINGS

Referring to the drawings.

BEST MODE OF CARRYING OUT THE INVENTION

Figure 1:
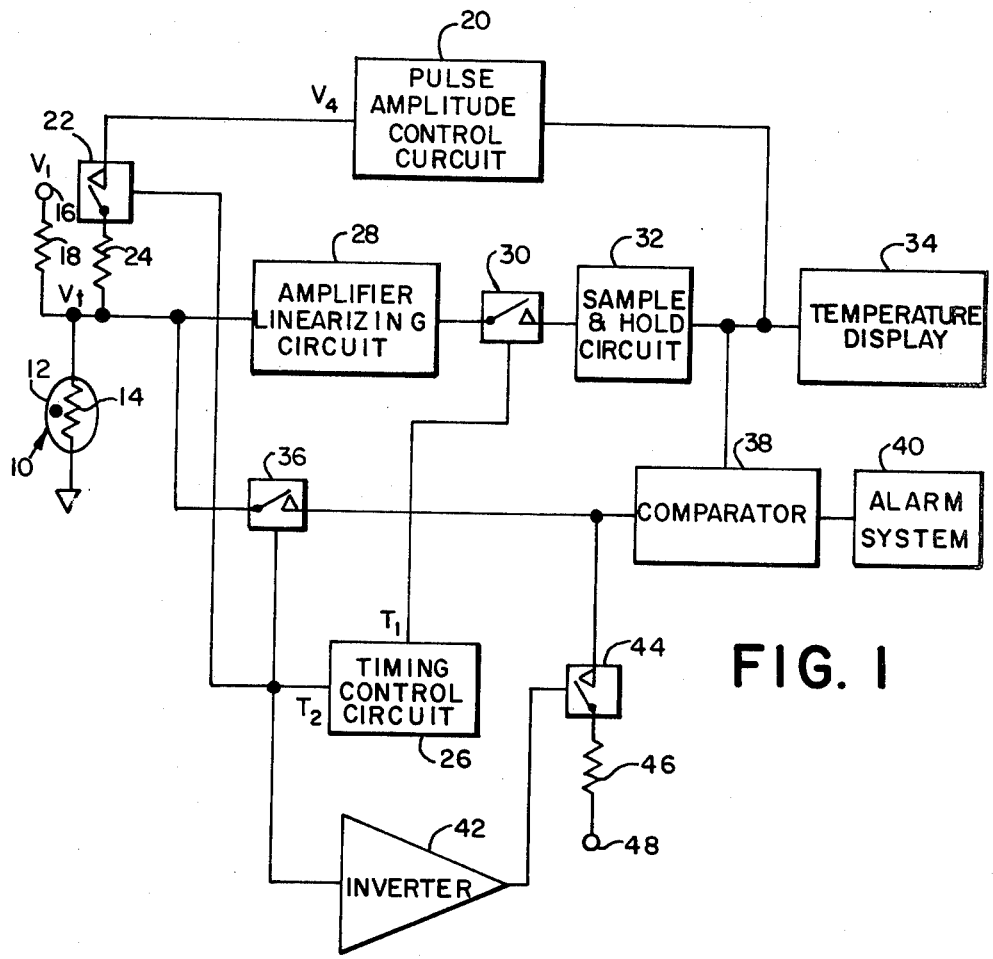
FIG. 1 is a circuit diagram of apparatus constructed in accordance with the present invention.
Figure 2:
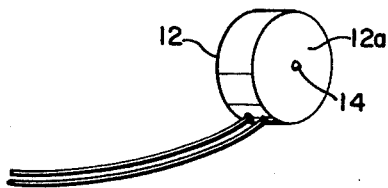
FIG. 2 is a perspective view of a temperature sensing probe which may be used in the FIG. 1 apparatus.

The apparatus illustrated in FIG. 1 shows the manner in which the present invention may be applied to indicate the dislodgement of a body temperature sensing probe from a body to which the probe has been attached. This apparatus includes a probe 10 having a probe housing 12 and a thermistor 14. As shown in FIG. 2, thermistor 14 is positioned in a contact surface 12a of the probe housing which is adapted for contact with a body. Thermistor 14 may be of conventional construction and operation. A BR14KA512J thermistor sold by Thermometrics, Inc. may be used. Such a device has a characteristic which varies as a function of its temperature. Specifically, thermistor 14 may have a negative temperature coefficient such that its electrical resistance varies inversely with the temperature to which the thermistor is exposed. As a voltage is applied to thermistor 14, a signal is developed across the thermistor which varies in accordance with its resistance, thereby providing an indication of the temperature to which the thermistor is exposed. The level of the applied voltage is such that the current flow produced is so small that the self-heating effect due to this current flow may be neglected.

Figure 3:
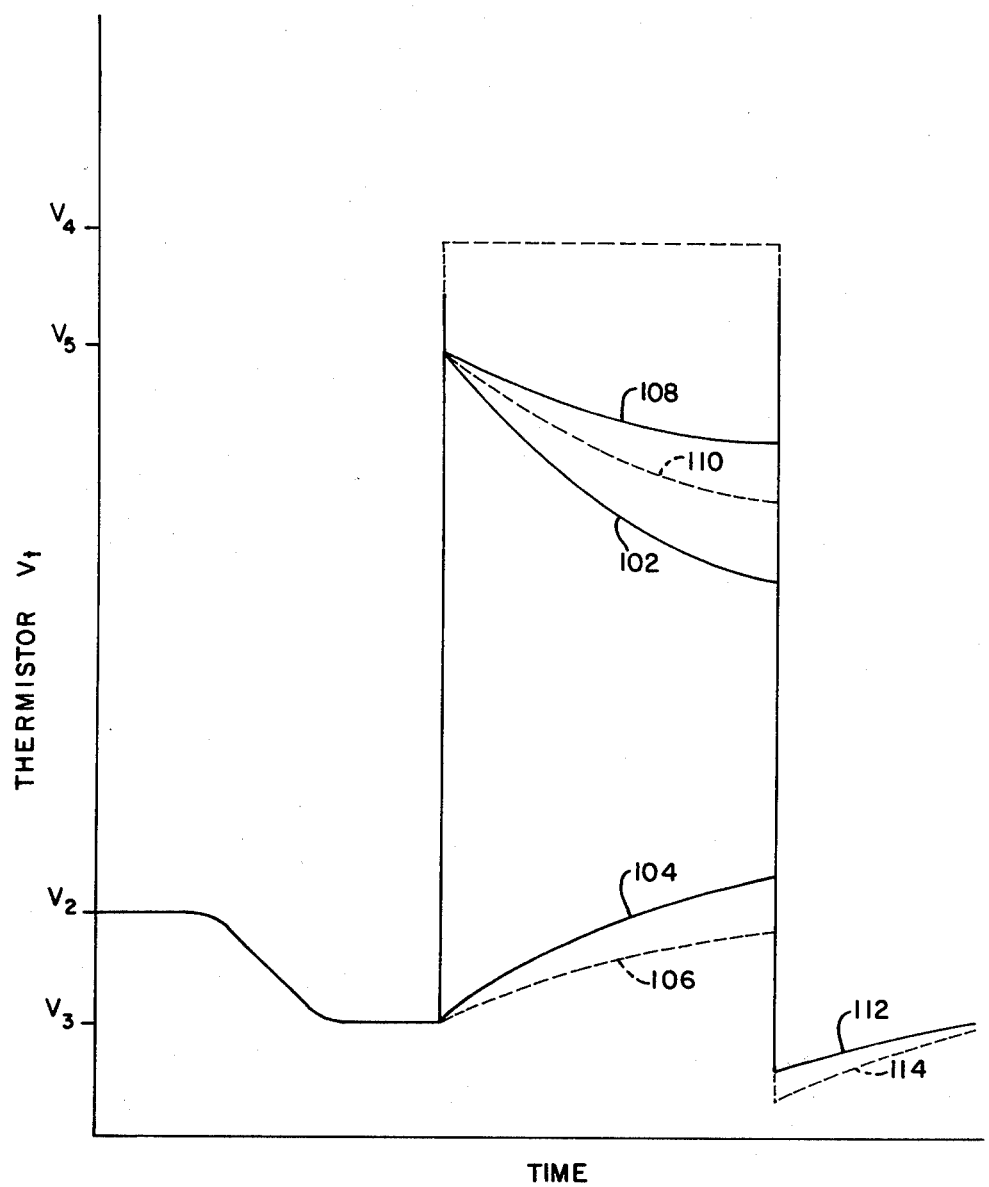
FIG. 3 is a waveform diagram useful in understanding the operation of the FIG. 2 probe.

Returning to FIG. 1, the apparatus also includes a source 16 of fixed voltage $V_1$ which is coupled to thermistor 14 through a current-limiting resistor 18. This arrangement produces a first signal component across thermistor 14 which is representative of the temperature of the body to which probe 10 is attached. FIG. 3 is a waveform diagram which shows the signal $V_t$ developed across thermistor 14. Voltage level $V_2$ represents the thermistor signal before attachment of probe 10 to a body. The difference between voltage $V_1$ and voltage $V_2$ is the voltage drop across current-limiting resistor 18.

After probe 10 is attached to a body having a temperature higher than the temperature to which thermistor 14 has been exposed, the increased temperature causes the resistance of the thermistor to drop, thereby reducing the thermistor signal $V_t$ to a voltage $V_3$. The gradual drop from voltage $V_2$ to voltage $V_3$ represents the thermal inertia of thermistor 14. The thermistor signal $V_t$ will vary with time as the temperature of the body to which probe 10 is attached varies. As the body temperature rises, signal $V_t$ drops. As the body temperature drops, signal $V_t$ rises. The signal across thermistor 14 will follow the temperature to which probe 10 is exposed fairly closely with only slight delays caused by the thermal inertia of the thermistor. Typically, source voltage $V_1$ and resistor 18 are selected to produce an operating voltage $V_3$ of about 0.5 V. Up to this point in the description of the invention, the temperature sensing function is in common practice at the present time.

The FIG. 1 apparatus further includes means for periodically heating thermistor 14 and for developing a control signal which is representative of such heating and the heat dissipated from the thermistor. Such means may include a pulse amplitude control circuit 20 which supplies a regulated voltage $V_4$ through an electronic switch 22 and a resistor 24 to thermistor 14. The action of switch 22 opening and closing develops a series of pulse signals which periodically heat thermistor 14. This produces a second signal component across thermistor 14 which is representative of the heating of the thermistor and the heat dissipated from the thermistor. The action of switch 22 is controlled by a timing control circuit 26 which will be described in greater detail hereinafter.

As seen from FIG. 3, the signal across thermistor 14 rises sharply to a level $V_5$ as the voltage from pulse amplitude control circuit 20 is coupled to thermistor 14 when switch 22 is closed. Voltage $V_4$ is shown in FIG. 3 by dot-dash lines. The difference between voltage $V_4$ and voltage $V_5$ is the voltage drop across resistor 24.

Decay curve 102 in FIG. 3 represents the effect of self-heating of thermistor 14 due to the application of voltage $V_5$ to the thermistor. As the thermistor temperature rises due to self-heating, the thermistor voltage drops. At the same time, thermistor 14 dissipates heat during the heating period. Rising curve 104 (solid line) represents the effect of heat dissipated from thermistor 14 with the thermistor in contact with a body, while rising curve 106 (dashed line) represents the effect of heat dissipated from the thermistor with the thermistor dislodged from the body. While in contact with a body, more heat is dissipated by thermistor 14, thereby tending to lower the thermistor temperature and causing a larger signal to be developed across the thermistor, than with the thermistor dislodged from the body. Decay curves 108 (solid line) and 110 (dashed line) show the net effects on the thermistor signal $V_t$ during the heating period for the thermistor in contact with the body and dislodged from the body. Curves 108 and 110 are derived by adding the two different effects of dissipation of heat from the thermistor to curve 102 which represents the self-heating effect due to the application of voltage $V_4$.

When switch 22 is opened, voltage $V_4$ is removed. This drives the thermistor signal $V_t$ downward to a level dependent upon the amount of heat dissipated by the thermistor during the time that voltage $V_4$ was applied. Thereafter, the thermistor signal $V_t$ rises to a level corresponding to the temperature to which the thermistor was exposed prior to the application of voltage $V_4$. The rate at which the thermistor signal $V_t$ rises to this level is dependent upon the dissipation of heat from the thermistor during the cooling period which follows the heating period. Rise curve 112 (solid line) represents the condition of the thermistor in contact with the body, while rise curve 114 (dashed line) represents the condition of the thermistor dislodged from the body.

From the foregoing, it is seen that the self-heating of thermistor 14 resulting from the application and removal of voltage $V_4$ provides a second signal component representative of the proximity of the thermistor to a body. Each pulse applied to the thermistor produces a positive-going portion during the heating period and a negative-going portion during the cooling period. The positive-going portion decays during the pulse at a rate dependent upon the dissipation of heat from the thermistor and the negative-going rises subsequent to the heating period also at a rate dependent upon the dissipation of heat from the thermistor.

Accordingly, the FIG. 1 apparatus includes means responsive to the second signal component of the thermistor signal $V_t$ for developing an indication of the proximity of the thermistor to a body to which it has been attached. Such means are effective to separate the first signal component and second signal component and to develop separate indications of body temperature and proximity of the thermistor to the body. Specifically, the thermistor signal $V_t$ is coupled through an amplifier and linearizing circuit 28, an electronic switch 30, and a sample and hold circuit 32 to a temperature display 34 where an indication of body temperature is developed. If probe 10 has been dislodged from the body, temperature display 34 will provide an indication of the temperature of the environment to which the probe is exposed.

The thermistor signal $V_t$ also is coupled through an electronic switch 36 to a comparator 38 where an indication of proximity of the probe to the body is developed. The output from sample and hold circuit 32 also is coupled to comparator 38.

Figure 4:
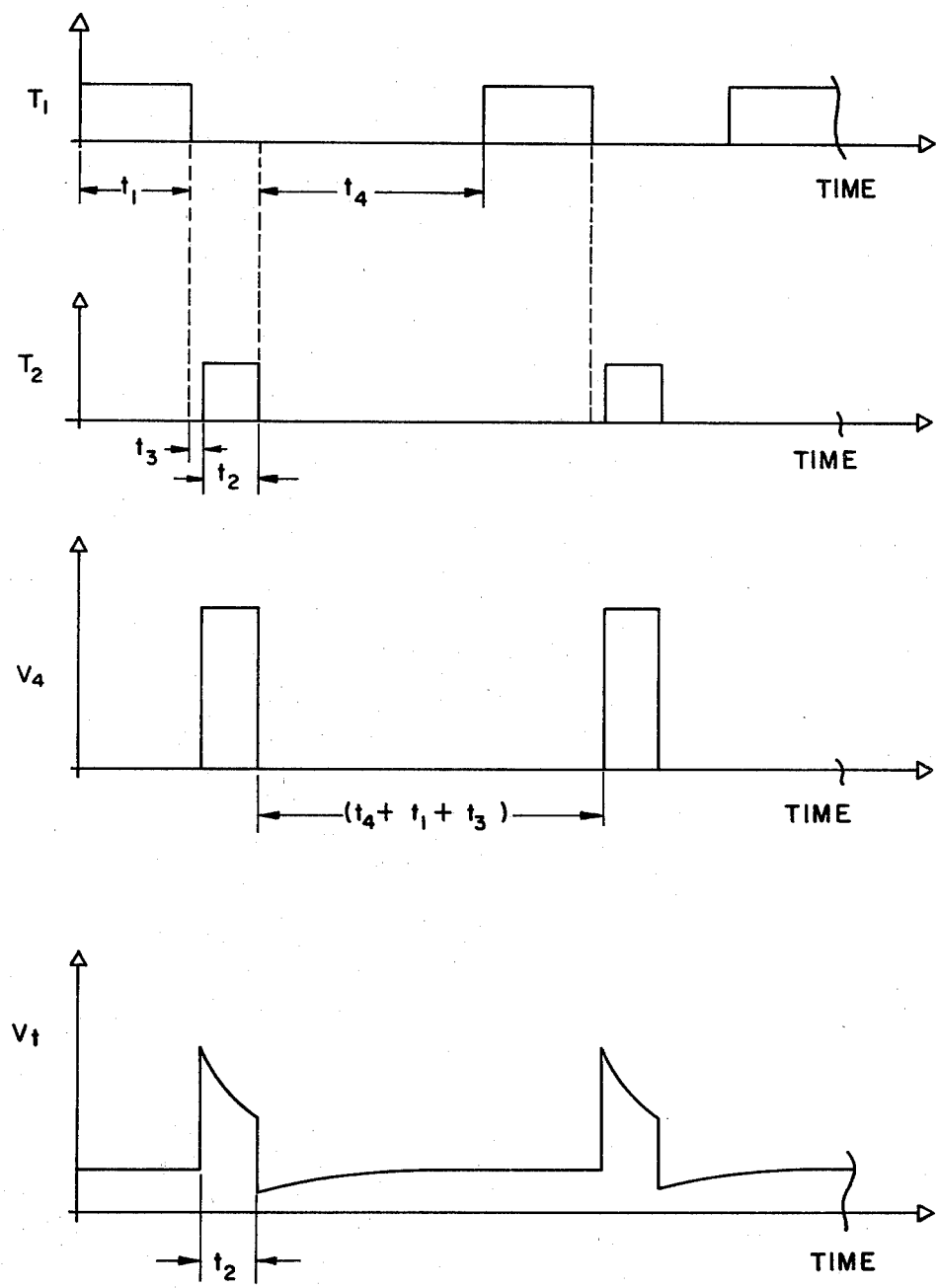
FIG. 4 shows a number of waveforms useful in understanding the operation of the FIG. 1 apparatus.

The operation of the FIG. 1 apparatus will be best understood by reference to FIG. 4. Timing control circuit 26 supplies a first series and a second series of timing control pulses $T_1$ and $T_2$. Timing control pulses $T_1$ control the the closing of switch 30, while timing control pulses $T_2$ control the closing of switches 22 and 36. During time $t_1$, when switch 30 is closed, the thermistor signal $V_t$ is supplied through amplifier and linearizing circuit 28 and switch 30 to sample and hold circuit 32. Amplifier and linearizing circuit 28 may be of conventional construction and operation in receiving the thermistor signal and processing it to put it in suitable form for further processing. Sample and hold circuit 32 also may be of conventional construction and operation in receiving a signal representative of the thermistor signal and storing this signal. As seen from FIG. 4, timing control pulses $T_1$ close switch 30 at times when the thermistor signal represents the temperature of the body to which probe 10 has been attached. Thus, the output of sample and hold circuit 32 represents either the body temperature component of the thermistor signal during the timing control pulses $T_1$ (time periods $t_1$) or the body temperature component of the thermistor signal stored during the last timing control pulse $T_1$.

During the closure of switches 22 and 36, the thermistor signal is supplied through switch 36 to comparator 38. Comparator 38 may be of conventional construction and operation in receiving two inputs and providing an output representative of the relationship of the inputs. As seen from FIG. 4, when timing control pulses $T_2$ close switch 22 during time periods $t_2$, positive-going signals are developed across the thermistor. These signals, riding on the body temperature component of the thermistor signal, are coupled through switch 36 to the lower input to comparator 38. As indicated above, the output of sample and hold circuit 32 is coupled to the upper input to comparator 38. The output signal from sample and hold circuit 32 serves as a reference in determining whether probe 10 has been dislodged from the body to which it has been attached. Amplifier and linearizing circuit 28 is designed to produce a signal from the thermistor signal which, during timing control pulses $T_1$, will fall between the two thermistor signal levels denoting that probe 10 is in contact with the body or that the probe has been dislodged from the body. Continuing with the example given above, if the thermistor signal $V_t$, at the beginning of time period $t_2$, is 5.0 V and is 4.8 V at the end of time period $t_2$ with the probe in contact with the body but is 4.6 V at the end of time period $t_2$ with the probe dislodged from the body, the reference signal from sample and hold circuit 32 is selected to be 4.7 V. For the condition of probe 10 remaining in contact with the body, the output from comparator 38 would be a positive 0.1 V, while for a loose probe condition, the output from the comparator would be a negative 0.1 V. The latter result would set off a suitable audible or visual alarm system 40.

Timing control circuit 26 may be of conventional construction and operation in providing accurately shaped timing pulses at the required frequency and relative timings. In order to assure that the proximity component of the thermistor signal $V_t$ does not pass through switch 30 to sample and hold circuit 32, a time period $t_3$ is provided between the end of time period $t_1$ and the beginning of time period $t_2$. The frequency of timing control pulses $T_2$ is selected to permit adequate cooling time of thermistor 14. Thus, an additional time period $t_4$ is provided, so that the total time between timing control pulses $T_2$ is $t_4 + t_1 + t_3$.

In order to prevent alarm system 40 from being set off falsely by the output of comparator 38 during the periods between timing control pulses $T_2$, an inverter 42, an electronic switch 44, a resistor 46 and source 48 of fixed voltage are provided in the FIG. 1 apparatus. These components are effective in disabling comparator 38 from developing an output signal which would signify a loose probe condition. Inverter 42 controls switch 44 to close the switch during the periods between timing control pulses $T_2$. When this occurs, the voltage from source 48 is coupled through resistor 46 and switch 44 to the lower input of comparator 38 such that the respective inputs to the comparator prevent the comparator from developing an output signal corresponding to a loose probe condition.

As seen in FIG. 1, the output of sample and hold circuit 32 is connected to pulse amplitude control circuit 20. This causes voltage level $V_4$ to track the body temperature last sampled before the initiation of a timing control pulse $T_2$. As a result, an equivalent amount of power is dissipated each time thermistor 14 is heated regardless of the thermistor resistance which varies with temperature.

The foregoing has set forth an exemplary and preferred embodiment of the present invention. It will be understood that various alternative embodiments will occur to those of ordinary skill in the art without departure from the spirit or scope of the present invention.

I claim:

1. Apparatus for indicating the dislodgement of an article from a body, said apparatus comprising:
   a temperature responsive element having a characteristic which varies as a function of its temperature, said element adapted for contact with a body for sensing the proximity of said element to said body;
   means for periodically heating said temperature responsive element and for developing a control signal which varies in accordance with said characteristic of said element and is representative of the heating of said element and the heat dissipated from said element, said control signal changing in level during the period of heating of said element at a rate dependent upon the dissipation of heat from said element during said period of heating;
   and means responsive to said control signal for developing during said period of heating of said temperature responsive element an indication of said proximity of said element to said body.

2. Apparatus according to claim 1 wherein said indication means include a comparison means responsive to said control signal and a reference signal for comparing said reference signal with the level of said control signal at the termination of said heating of said temperature responsive element.

3. Apparatus according to claim 2 further including a probe housing within which said temperature responsive element is positioned.

4. Apparatus according to claim 2 wherein said control signal includes a positive-going portion which decays during said heating of said temperature responsive element.

5. Apparatus according to claim 1 wherein successive periods of heating of said temperature responsive element are spaced apart in time to permit said temperature responsive element to dissipate all its heat.

6. Apparatus for sensing body temperature comprising:
- a probe housing having a contact surface adapted for contact with a body;
- a thermistor having an electrical resistance which varies as a function of its temperature, said thermistor positioned within said contact surface of said probe housing for sensing the temperature of said body and for sensing the proximity of said thermistor to said body;
- a source of fixed voltage;
- means for coupling said fixed voltage source to said thermistor to develop across said thermistor a first signal component representative of said temperature of said body;
- a source of pulse signals;
- means for coupling said pulse signal source to said thermistor to periodically heat said thermistor and to develop across said thermistor a second signal component which varies in accordance with said electrical resistance of said thermistor and is representative of the heating of said thermistor and the heat dissipated from said thermistor, said second signal component changing in level during the period of heating of said thermistor at a rate dependent upon the dissipation of heat from said thermistor during said period of heating;
- means coupled to said thermistor for separating said first and said second signal components;
- means coupled to said separating means and responsive to said first signal component for developing an indication of said temperature of said body;
- and means coupled to said separating means and responsive to said second signal component for developing during said period of heating of said thermistor an indication of said proximity of said thermistor to said body.

7. Apparatus according to claim 6 wherein said means which develop said proximity indication include a comparison means responsive to said second signal component and a reference signal for comparing said reference signal with the level of said second signal component at the termination of said heating of said thermistor.

8. Apparatus according to claim 7 wherein said first signal component is said reference signal and said separating means include means for coupling said first signal component to said comparison means.

9. Apparatus according to claim 8 wherein said pulse signals source includes a second voltage source and a switch which is opened and closed to generate pulses.

10. Apparatus according to claim 9 wherein said separating means controls the opening and closing of said switch.

11. Apparatus according to claim 10 wherein said first signal component is coupled to said second voltage source to control the amplitude of said pulses.

12. Apparatus according to claim 6 wherein successive periods of heating of said thermistor are spaced apart in time to permit said thermistor to dissipate all of its heat.

13. Apparatus for sensing body temperature comprising:
- a probe housing having a contact surface adapted for contact with a body;
- a thermistor having an electrical resistance which varies as a function of its temperature, said thermistor positioned within said contact surface of said probe housing for sensing the temperature of said body and for sensing the proximity of said thermistor to said body;
- a source of fixed voltage;
- means for coupling said fixed voltage source to said thermistor to develop across said thermistor a first signal component representative of said temperature of said body;
- a source of pulse signals;
- means for coupling said pulse signals source to said thermistor to periodically heat said thermistor and to develop across said thermistor a second signal component which varies in accordance with said electrical resistance of said thermistor and is representative of the heating of said thermistor and the heat dissipated from said thermistor, said second signal component changing in level during the period of heating of said thermistor at a rate dependent upon the dissipation of heat from said thermistor during said period of heating;
- means responsive to said first signal component for developing an indication of said temperature of said body;
- and means responsive to said second signal component for developing during said period of heating of said thermistor an indication of said proximity of said thermistor to said body.

* * * * *

UNITED STATES PATENT AND TRADEMARK OFFICE
CERTIFICATE OF CORRECTION

PATENT NO. : 4,399,823
DATED : August 23, 1983
INVENTOR(S) : MICHAEL M. DONNELLY It is certified that error appears in the above—identified patent and that said Letters Patent is hereby corrected as shown below:

In Column 8, line 23, cancel "of" and substitute --to--.

Signed and Sealed this

Tenth Day of January 1984

[SEAL]

Attest:

GERALD J. MOSSINGHOFF

*Attesting Officer*   *Commissioner of Patents and Trademarks*